United States Patent [19]

Antonik

[11] Patent Number: 4,490,360
[45] Date of Patent: Dec. 25, 1984

[54] FIREFLY-DERIVED REPELLENT COMPOSITIONS AND METHODS OF USE

[75] Inventor: Steven J. Antonik, St. Louis, Mo.

[73] Assignee: Duke University, Durham, N.C.

[21] Appl. No.: 399,265

[22] Filed: Jul. 19, 1982

Related U.S. Application Data

[63] Continuation-in-part of Ser. No. 103,341, Dec. 13, 1979, Pat. No. 4,340,587.

[51] Int. Cl.³ .............................................. A01N 63/02
[52] U.S. Cl. ............................... 424/95; 424/DIG. 10
[58] Field of Search ........................... 424/95, DIG. 10

[56] References Cited

U.S. PATENT DOCUMENTS 4,340,587  7/1982  Antonik ...................... 424/DIG. 10

OTHER PUBLICATIONS

Bulletin of the Bureau of Standards vol. 6 (1909–1910) pp. 321–336 Ives et al., "Luminous Efficiency of the Firefly".
Tsujimoto; Chemical Abstracts vol. 23 (1929) p. 1443.
J. Copeland, "Effects of larval firefly extracts on molluscan cardia activity," *Experientia* 37 (1981) Birkhäuser Verlag, (Schweiz).
J. Meinwald et al., "Lucibufagins. 2. Esters of 12-Oxo-$2\beta$, $5\beta$, 11 $\alpha$-trihydroxybufalin, the Major Defensive Steroids of the Firefly *Photinus pyralis* (Coleoptera: Lampyridae)," *Journal of the American Chemical Society*, vol. 101:11, (1979), pp. 3055–3010.
M. A. Goetz et al., "Lucibufagins, IV. New defensive steroids and a pterin from the firefly *Photinus pyralis* (Coleoptera: Lampyridae)," *Experientia*, vol. 37:7 (1981) pp. 679–788.
T. Eisner et al., "Lucibufagins: Defensive steroids from the fireflies *Photinus ignitus* and *P. marginellus* (Coleoptera: Lampyridae)," *Proc. Natl. Acad. Sci.*, vol. 75:2 (1978), pp. 905–908.
T. Eisner et al., "Toxicity, Odor Aversion, and 'Olfactory Aposematism'," *Science*, vol. 213, Jul. 25, 1980, p. 476.

*Primary Examiner*—Leonard Schenkman
*Assistant Examiner*—Joseph A. Lipovsky
*Attorney, Agent, or Firm*—Oblon, Fisher, Spivak, McClelland & Maier

[57] ABSTRACT

A naturally derived repellent composition for organisms which contains as the active ingredient an effective amount of a firefly-derived constituent and methods for using same to repel organisms.

16 Claims, No Drawings

FIREFLY-DERIVED REPELLENT COMPOSITIONS AND METHODS OF USE

CROSS-REFERENCED TO RELATED APPLICATIONS

This application is a continuation-in-part of application Ser. No. 103,341, to Steven J. Antonik, filed Dec. 13, 1979, now U.S. Pat. No. 4,340,587.

BACKGROUND OF THE INVENTION

1. Field of the Invention

This invention relates to firefly-derived compositions useful in repelling various organisms from areas where their presence is dangerous or undesirable and methods of using these compositions.

2. Description of the Prior Art

During a research program carried out to investigate medical and related properties of fireflies (*Photinus pyralis*, the North American Black Firefly) and firefly dispersions, extracts, and lyophilized lanterns, bodies, and component parts of fireflies, it was discovered that preparations made from the fireflies exhibited the unexpected property of acting as repellents for various types of organisms. In the above-referenced application Ser. No. 103,341, it was demonstrated that these firefly-derived compositions were efficacious against pinfish (*Lagodon rhomboides*) and the Atlantic sharpnosed shark (*Phizoprinodon terraenoval*) when used in concentrations as low as one firefly per liter. In a paper presented at the symposium entitled, "Problems and Possibilities: The Development of an Effective Shark Repellent for Naturally Occurring Biologically Active Substances", Jan. 5, 1981, at the Annual Meeting of the American Association for the Advancement of Science in Toronto, Canada, Bonaventura et al disclosed the results of work done on the use of firefly-derived repellents against the Atlantic Sharpnosed Shark (*Rhizoprinodon terraenovae*), the smooth dogfish (*Mustelus canis*), the pinfish (*Lagadon rhomboides*), and Killifish (*Fundulus heteroclitus*). Toxic and behavioral effects were noted with all test organisms. In experiments involving dispersed fireflies at a concentration of 4 fireflies per liter, rapid behavior responses in the elasmobranchs were noted. In every instance significant repellent activity of the firefly-derived compositions was demonstrated. Spurred on by the encouraging results of the tests done against the various fish species, additional research has been carried out in an effort to establish a much broader scope of utility for the firefly-derived repellent compositions.

SUMMARY OF THE INVENTION

It is an object of this invention to develop a naturally derived repellent composition.

It is another object of this invention to develop a naturally derived repellent composition having a broad spectrum of utility, that is, effective against a variety of organisms.

It is a further object of this invention to develop a method for repelling dangerous or annoying organisms.

It is yet a further object of this invention to develop a method for repelling dangerous or annoying organisms which is inherently not harmful to the environment in which it is being used.

These and other objects of the invention, as will herinafter become more readily apparent, have been accomplished by a naturally derived repellent composition for organisms which contains as the active ingredient an effective amount of a firefly-derived constituent.

DESCRIPTION OF THE PREFERRED EMBODIMENTS

The repellent compositions of this invention are derived from fireflies and include all members of the insect genus Photinus. Representative of the species within said genus include, but are not limited to, *pyralis, pennsylvanica, marginellus* and *scintillans*. The repellent compositions are derivatives from fireflies and include but are not limited to dispersions, suspensions, dried powders, and extracts of whole fireflies, firefly lanterns, firefly bodies excluding lanterns, the various component parts of fireflies, and mixtures thereof.

The repellent compositions may be prepared by homogenizing whole fireflies, firefly lanterns, firefly bodies excluding lanterns, the various component parts of fireflies, and mixtures thereof in water or a polar organic solvent such as ethanol. Alternatively, the firefly components listed above may be homogenized and then dried or lyophilized using conventional techniques and stored for subsequent use.

It is also been discovered that the active ingredient of fireflies can be extracted with a suitable organic solvent by homogenizing the firefly components in the presence of said solvents at room temperature for a suitable period of time, one hour being sufficient, and then separating the solvent solution from the solids portion by filtration or other well known liquid-solid separation techniques. Suitable solvents for extraction of the active ingredient include the non-polar solvents examples of which include, but are not limited to, chloroform, 1,1,1,-trichloroethane, 1,1,2,2-tetrachloroethane, carbentetrachloride, benzene, toluene and cyclohexane.

The firefly-derived repellent compositions of this invention may be applied by spraying dispersions or suspensions containing homonogenized whole firefly, firefly lanterns, firefly bodies excluding lanterns, the various component parts of fireflies or mixtures thereof onto the area or objects from which the organisms are to be repelled. The suspensions and dispersions may be prepared by homogenizing whole firefly bodies, firefly lanterns, firefly bodies absent lanterns, the various component part of fireflies or mixtures thereof in water or a suitable polar solvent such as ethanol. It has been found advantageous, but not required to include an effective amount of a surface active agent carrying the suspensions and dispersions. Suitable surface active agents include the cationic surfactants, amionic surface active agents and non-ionic surface active agents. A preferred surface active agent is triton-X-100. The surfactants are added in amounts of less than 2%. The suspensions and dispersions may contain from 0.04 to 8 or more grams of firefly bodies per liter of carrier liquid and continued to demonstrate repellent characteristics many weeks after the carrier has evaporated.

Alternatively, the previously dried or lyophilized firefly-derived constituents may be suspended or dispersed in water or a polar organic solvent such as ethanol, with or without surfactant addition, and then applied as a spray, the repellent effects being the same.

The firefly-derived repellent compositions of this invention may also be applied by spraying organic solvent solutions containing the extracted active ingredient. Such solvent solutions containing the extract of 0.04 to 8 or more grams of firefly bodies per liter of solution have been found to be effective.

The dried or lyophilized firefly constituents may also be applied directly by dusting with a finely divided powder of said dried or lyophilized constituent, with or without an inert solid, finely divided carrier such as talc or silica.

As disclosed in copending patent application Ser. No. 103,341, filed Dec. 13, 1979, the firefly-derived repellent compositions of this invention may be used to repel marine organisms, such as sharks and pinfish. When used for this purpose, the repellent compositions are introduced as aqueous dispersions into the zone of exclusion in concentrations of 1 to 4 firefly bodies per liter. It has also been found that the repellent compositions may be added in the form of hydrophilic polymerized foams containing the firefly-derived component, thereby providing a effective repellency over an extended period of time. These hydrophilic polymerized foams are disclosed in U.S. Pat. No. 3,929,574 issued to Wood et al on Dec. 30, 1975.

The organisms for which the firefly-derived composition of this invention have proved effective include insects, fish, birds and mammals.

Within the class Insecta, the following orders have been found to respond to the firefly-derived compositions of this invention:

Leptodoptera, the moths and butterflies, including their larvae;
Coleoptera, the beetles, such as flour beetles;
Orthroptera, the cockroaches, crickets, and grasshoppers;
Isoptera, the termites; and
Homoptera, the soft bodied insects such as aphids.

The marine animals contemplated within the scope of this invention are the fish of the class Chondrichthyes, the cartilagimons fish such as sharks, and the class Osteichthyes, the bony fish such as the teleosts. Specific marine animals responding to the repellent compositions of this invention include but are not limited to the Atlantic sharpnose shark, *Rhizoprinodon terraenovae*, the smooth dogfish, *Mustelus canis*, the pinfish, *Lagadon rhomboides*, and Killifish, *Fundulus heterocilitus*.

Birds contemplated to be within the scope of this invention include all birds within in the Class Aves, the Orders Anas, Larus, Columba, Gallus, Turdus, Dendroica, Sturnus, Passer, and Mellspiza. Specific birds include but are not limited to pigeons and crows.

Organisms within the class Mammalia include those mammals within the orders Lagomorpha, Rodentia, and Carnivora and include rabbits, rodents, cats and dogs.

Having now generally described this invention, the same would be better understood by reference to certain specific examples, which are included herein for purposes of illustration only and are not intended to be limiting of the invention or any embodiment thereof, unless specified.

A series of experiments were conducted with solutions of firefly extract to determine if these materials may have some activity against avian and mammalian species. Studies involved the application of the extract to nesting materials, foodstuffs and roosting areas. Mammal species utilized in these tests were: *Peromyscus leucopus* (white-footed mouse), *Rattus norvegicus* (albino Norway rats), *Mus musculus* (House mouse) and *Columba livia* (pigeon). The extract solutions were aqueous solutions with a concentration of 2 grams/Liter of lyophilized firefly. The results appear as Experiments 1-5.

EXAMPLE 1

White-footed mice *Peromyscus lecopus* which were housed in captivity were utilized in this initial study. These animals were placed in an enclosure approximately 2×3 feet. Food and water were made available. Two nesting boxes (8"×12"×6") were supplied to the animals. A layer of corn cob bedding was placed on the floor of the enclosure to a depth of approximately 1 inch. A commercially available nesting material (Nestlets-cotton fiber) were placed into the nesting boxes and animals were allowed to shred the material and form nests within these boxes. A total of twenty mice were housed in the enclosure. On Day 1 the nesting material was sprayed. The box which has the most animals in it was selected for treatment with the firefly extract (aqueous). Over two-thirds of the test population were within this box at the time of application. One ounce of the extract was sprayed onto the nesting material of this preferred box using a Crown Spray tool. The second box was left untreated and served as a control. Daily visual observations were conducted to determine the number of animals which were in each of the boxes. The results are as follows:

| Day | Number in Treated Box | Number in Untreated Box |
| --- | --- | --- |
| 2 | 1 | 19 |
| 3 | 3 | 17 |
| 4 | 0 | 20 |
| 5 | 6 | 14 |
| 6 | 3 | 17 |
| 7 | 3 | 17 |
| 8 | 4 | 16 |
| 9 | 4 | 16 |
| 10 | 4 | 16 |
| 11 | 4 | 16 |
| 12 | 8 | 12 |
| 13 | 14 | 6 |

EXAMPLE 2

Two female albino Norway rats (*Rattus norvegicus*) were placed in an enclosure approximately 2'×3'. The floor of the enclosure was covered with a commercially available bedding material (Bed-o-Cobs—corncob derived bedding material) to a depth of approximately 1". Three nesting boxes, similar in dimensions to those used in Example 1 were provided for the animals to nest in. Two of these boxes, which were located along the walls, had the tops removed so that treated bait could be easily observed at treatment. Animals were then fasted for 24 hours prior to test.

One TALON ™ Rodenticide bait pack was opened and the contents placed in a clean bowl. A small quantity of agitated firefly extract (aqueous) was dripped onto the pellets. The pellets were stirred as the material was added. These pellets were then placed back into the place pack from it was originally removed and sealed while the pellets were still wet.

The treated bag was marked on both sides to aid in identification. The treated bag was then placed in one uncovered station with an untreated bag similarly placed in the opposite end of the enclosure. Initial weights of the placepack at the time of placement are as follows:

Treated Place Pack: 54.2 g

Untreated Place Pack: 54.0 g

Results

At 09:00 hours on the day following placement of the packs into the enclosure near total consumption of both packs had occurred. Place pack penetration by the rats appeared to be equal. Only an occasional pellet was detected in the bedding but insufficient quantities remained for collection and reweighing. The experiment was at this point terminated and all animals sacrificed.

EXAMPLE 3

2.0 ml of each form of extract (aqueous, acetone, surfactant) were added to the contents of TALON place packs. Each sample was allowed to air dry for 23 hours. The samples were then placed back into the original placepack and sealed. Weights of the various samples are as follows:

|     | Aqueous Extract | | Acetone Extract | | Surfactant Extract | |
| --- | --- | --- | --- | --- | --- | --- |
| Day | T | C | T | C | T | C |
| 2 | 0 | 0 | 0 | 0 | * | * |
| 3 | 0 | 0 | 0 | 0 | Same | Same |
| 4 | 0 | 0 | 0 | 0 | 27.3 | 54.3 |
| 5 | * | 0 | 0 | 0 | Same | Same |
| 6 | 25.6 | 0 | 0 | 0 | " | " |

Numeral = amount consumed
0 = unopen
* = penetrated but no take

EXAMPLE 4

One group of 5 male and 5 female House mice (*Mus musculus*) which were recently captured were selected for this experiment. Each animal was sexed and weighed prior to the release into the test enclosure. All were visually assessed for external signs of health, (i.e., appearance of coat). The mice were tested under similar conditions as described in Example 1 except that the control station was sprayed with a similar amount of tap water. Approximately 1 ounce of aqueous extract was sprayed on the treatment nesting material and a similar amount of water was sprayed on the control nesting material. Results are as follows:

| Day | Number of Mice in Treated Box | Number of Mice in Control Box |
| --- | --- | --- |
| 1 | 9 | 1 |
| 2 | 7 | 3 |
| 3 | 8 | 2 |
| 4 | 8 | 1* |
| 5 | 8 | 2** |

*one animal found in food bowl - nesting
**one animal found dead in extract sprayed box. The mouse had been partially consumed by the remainder of mice in the enclosure. This mouse appeared to be a submissive male but numerous wounds appeared to be fresh on the hindquarters of the animal.

EXAMPLE 5

A group of approximately 35 feral pigeons (*Columba livia*) were used in an evaluation of the firefly extract (aqueous). The pigeons were housed in an enclosure that was approximately 20'(l)×8'(W)×8'(H), and was divided into three separate areas. These areas were connected by doors which were kept open at all times. Purina Pigeon Checkers, a commercially pigeon diet, and water were available to the birds at all times. Water was offered to the birds via a five gallon chicken waterer. Food and water were placed in the central area and birds had access to all three of the areas within the enclosure.

In the outer two areas there was a window which offered a ledge to the birds. On these ledges a device containing 2 MDL Motion Detectors was mounted to make observation of the roosting activities of these pigeon. These devices measure the combination of head and body movement by way of an infared cell as described by Kaukeinen (1979) in ASTM STP 680, pages 68-83. The units were mounted facing from the outer side of the ledge toward the inside of the enclosure. These were monitored on a daily basis. For four days the activity around the ledges was noted prior to application of the treatment. After the activity levels were monitored on the fourth day the ledges were selected to receive either the treatment or the control application. The window to receive treatment was selected randomly. Immediately prior to the treatment the ledges were thoroughly scraped of fecal material. The left side of the enclosure was treated with the aqueous extract solution while the right side of the enclosure was treated with tap water. Both were applied to the point of run-off. Results are as follows:

| | Right Ledge | | | Left Ridge | | |
| --- | --- | --- | --- | --- | --- | --- |
| Date | Front Sensor | Back Sensor | Total | Front Sensor | Back Sensor | Total |
| 6/14 | 35 | 25 | 60 | 1303 | 6 | 1309 |
| 6/15 | 25 | 31 | 56 | 44 | 11 | 55 |
| 6/16 | 48 | 42 | 90 | 14 | 86 | 100 |
| 6/17 | 46 | 0 | 46 | 7 | 48 | 55 |
| Treatment Begins: | | | | | | |
| 6/18 | 33 | 32 | 65 | 6 | 43 | 49 |
| 6/19 | 20 | 6 | 26 | 1 | 10 | 11 |
| 6/20 | 45 | 14 | 49 | 11 | 32 | 43 |
| 6/21 | 23 | 7 | 30 | 0 | 10 | 10 |
| 6/22 | 66 | 31 | 97 | 14 | 52 | 66 |
| 6/23 | 45 | 13 | 58 | 10 | 16 | 26 |
| 6/24 | 38 | 8 | 46 | 3 | 11 | 14 |
| 6/25 | 5 | 2 | 7 | 3 | 10 | 13 |
| 6/26 | 20 | 9 | 29 | 3 | 29 | 32 |
| 6/27 | 12 | 5 | 17 | 0 | 11 | 11 |

It is to be noted that the pigeons seemed to prefer the left ledge prior to treatment and showed a clear preference for the untreated right ledge subsequent to treatment.

EXAMPLE 6

Subjects—Common wild field mice taken from vacant fields in Elk Grove Township.

Materials—Schleicher & Schueller filter paper cards (3"×3") impregnated with whole swine blood spots. Firefly extract composed of pulverized, lyophilized firefly lanterns (tails)—one lantern then combined with 5 ml of distilled water. Two cards with spots were saturated with the firefly extract combination and two were untreated.

Method—The mice were exposed to the treated and untreated cards in a random order over a two day period with unlimited access to the cards.

Results—The mice would eat the dried swine blood on the untreated cards but would avoid the treated cards. No sign of damage from the mice was observed on the treated cards which contained identical amounts of dried blood and were in identical positions of access.

EXAMPLE 7

The repellant effects of aqueous dispersion of lyophilized firefly on the common crow, Corvus brachyrhynchos, were tested in the following way. Crows were observed feeding on fallen olives in an olive grove. Two bed sheets were spread out in the olive grove and one was sprayed with the aqueous solution and allowed to dry while the other sheet was left untreated. When the treated sheet had dried completely, dropped olives were collected and spread on the two sheets. The feeding habits of the crows were observed for several hours. No crows would feed off the treated sheet but demonstrated no reticense about eating the olives on the untreated sheet.

EXAMPLE 8

The repellant effects of aqueous dispersions of ground up whole fireflies on Gypsy Moth caterpillers was demonstrated as follows.

Twelve whole fireflies were ground up and added to about a pint of water. An avocado tree and a bush of unknown variety, both heavily infested with gypsy moth caterpillers, were sprayed on successive days. All predation on the sprayed tree and bush by the gypsy moth caterpillers ceased, but continued on the other untreated flora in the area.

EXAMPLE 9

The repellant effects of firefly suspension on Confused Flour Beetle and their larvae was demonstrated as follows.

Five Petri dishes, divided into quadrants, were used for containment and exposure. In Dish No. 1, the five beetles were placed into opposite quadrants that contained no flour. To both sides, the quadrant contained flour. In one quadrant, the flour was mixed with the suspension and the other quadrant's outer edge was coated with the suspension. In the second dish, the two floured quadrants were both lined with the suspension and the beetles were placed in the unfloured sections. In Dish No. 3, the beetles were placed in flour that was exposed to firefly suspension but there was no suspension in the floured section opposite where they were placed.

In Dishes Nos. 4 and 5, the larvae of the beetles were exposed to the suspension. This was to see how the suspension may affect the growth and maturity of the larvae. In Dish No. 4, five beetles in the larval stage were placed into the flour that was exposed to the suspension but they also had the non-exposed flour for an outlet. In Dish No. 5, ten larvae were placed into all sections which had the suspension mixed into the flour.

An observation was made every 24 hours for four days. It was evident that the activity and motivation of the beetles and their larvae were affected.

EXAMPLE 10

The repellant effects of compositions of this invention on cats was investigated.

Subjects—Two shell type lounge chairs, identical in nature. Covered with identical types of solid color rough testured upholstery fabric. An ordinary window spray container and push type spray dispenser with the aparture enlarged to permit the disbursement of particulate matter. Six whole lyophilized fireflies pulverized and suspended by shaking in four fluid ounces of tap water.

Method—One chair was sprayed with the firefly matter-water combination and the other chair did not receive any treatment. The chairs were separated by an 18 inch wide table. Room temperature varied between 65° to 75° F. All materials were applied and allowed to air dry which occurred in one day.

Observations—Both chairs were used by both cats daily for lounging and sleeping prior to the date of treatment with a distinct preferance by the male cat for the treated chair. The female had been introduced to the household in March, 1980 and has continued to exhibit typical claw sharpening activity using furniture and scratching boards.

Results—For the first three days after treatment, the male would climb onto the treated chair but only remain there for no more than three minutes. The female did not approach the chair to lounge or scratch the fabric after treatment was applied. After the third day, the male has also avoided the chair and this behavior has continued to the date of this writing, more than 8 months. No odor from the material was observed and no damage or spotting of the light colored fabric was noticed. The cats remained healthy and active throughout.

EXAMPLE 11

In a separate cat experiment, two spots in a home were sprayed with aqueous solutions of repellant in a concentration of 2 grams of lyophilized firefly in 100 ml $H_2O$. The cats noticeably avoided the two sprayed areas which were their normal scratching spots.

EXAMPLE 12

A series of tests were carried out on pinfish (*Lagodon rhomboides*). Whole, lyophilized fireflies were ground in a tissue homogenizer and suspended in seawater. Using an eight liter experimental tank containing pinfish, whole firefly "toxin" or repellant was introduced at a concentration providing one firefly per liter of seawater. The reactions of the pinfish were then observed over a period of one hour, the observations being recorded in Table I set forth below:

TABLE I

| TIME (Mins.) | OBSERVATIONS |
| --- | --- |
| 0 | distress, rapid irregular and random "darting", confusion |
| 7 | labored breathing, continued eratic swimming |
| 11 | the usual white appearance is gone, true colors returning |
| 12:45 | loss of balance |
| 15 | slow breathing, inactivity |
| 20 | increased activity, swimming fast |
| 21 | hyperventilation |
| 28 | rapid hyperventilation |
| 31 | movement of all fins, increased hyperventilation |
| 40 | no movement other than breathing |
| 45 | no change |
| 51 | loss of ability to swim, slowed down breathing |
| 56 | no change |
| 60 | no change |

EXAMPLE 13

Similar experiments were carried out at concentrations corresponding to two fireflies per liter of seawater and four fireflies per liter. The observed results are set forth below in Examples 2 and 3 in the tables below:

TABLE II (Two fireflies per liter)

| TIME (Mins.) | OBSERVATIONS |
|---|---|
| 0 | darting, pin-dorsal fin up, confusion |
| 7 | rapid breathing, loss of balance |
| 10 | loss of ability to swim, very rapid breathing |
| 15 | loss of ability to swim, slower breathing |
| 20 | loss of ability to swim, slow breathing, total inactivity |
| 30 | no change, slight fin movement |
| 40 | no change, slight fin movement, labored breathing |
| 50 | (same as 40 minutes) |
| 55 | no change, more fin movement |
| 60 | very labored breathing, more fin movement |

EXAMPLE 14

TABLE III (Four fireflies per liter)

| TIME (Mins.) | OBSERVATIONS |
|---|---|
| 0 | confusion, darting |
| 5 | Rapid Breathing |
| 10 | Inactive, loss of balance |
| 15 | Hard breathing, some darting |
| 20 | Hard breathing, some darting |
| 25 | Agitation, still has ability to swim |
| 30 | Agitation, still has ability to swim |
| 35 | No movement, still has ability to swim |
| 40 | No movement, still has ability to swim |
| 45 | Agitated, breathing, still has ability to swim |
| 50 | Agitated, slow breathing, has ability to swim |
| 55 | Slowed breathing, still has ability to swim |
| 60 | Inactive, slowed breathing, has ability to swim |

It is evident from a consideration of the recorded data that even at a concentration as low as one firefly per liter, the pinfish exhibited marked distress, disruption in breathing habits, color modifications, increased activity, hyperventilation, and even loss of ability to swim. The effect produced appears clearly to be a function of the concentration, more disruptive effects being evident at the higher concentration of fireflies in the seawater.

EXAMPLE 15

A similar test was carried out on the Atlantic Sharpnose Shark (*Phizoprinodon terraenoval*). The concentration of fireflies was four fireflies per liter of seawater. Again, as recorded in the table below, the shark exhibited marked reactions including hysteria, effects on respiration, chaotic movements, and rapid eye movement, all indicating a significant sensitivity to the agent introduced into the seawater.

TABLE IV

| TIME (Mins.) | OBSERVATIONS |
|---|---|
| 0 | massive hysteria |
| 10 | calmed down, breathing accelerated |
| 20 | circular swimming, breathing accelerated |
| 30 | no movement, rapid hyperventilation |
| 40 | no movement, rapid hyperventilation |
| 50 | very rapid hyperventilation, chaotic movements followed by no movement |
| 60 | very rapid hyperventilation, no movement, REM (rapid eye movement) |

EXAMPLE 16

The repellant of lipid extract of firefly on killifish, *Fundulus heteroclitus*, was determined as follows.

Lipids were extracted from 20 grams wet weight whole firefly using the classic Bligh-Dyer extraction method which employed a biphasic system containing methanol, chloroform and hydrated tissue in 2:1:0.8 ratio. The chloroform phase containing the lipid was dryed under nitrogen and resuspended in 95% ethanol. The aqueous layer was bubbled with nitrogen for one hour.

A preference tank was constructed from a 4 foot length of 3 inch diameter white PVC pipe. The pipe was sliced lengthwise in half to produce a 4 liter trough. Fittings for tubing leading to an Orion research pipette pump were sealed in place at each end of the trough. The pipette pump was adjusted to the desired flow rate of 1.2 ml/min. which allowed the slow flow of different fluids into the ends of the trough. The tank drained through small holes at the high water line in the middle of the tank. This system in theory produces a chemical gradient controlled by the injected fluid flow rate and concentration.

The tank was filled with 4 liters of clean sea water and the flow rates of injected sea water set at 1 ml/min. One killifish was placed in the middle of the tank and observed for 15 minutes. Next ethanol-lipid extract from 20 grams whole fireflies was introduced at a rate of 1 ml/min. at one end and pure ethanol was introduced at the other end. The behavior of the fish, notably the percentage of time the fish hovered near a 3 inch area at either end was recorded over a 15 minute interval. The tank was then washed with soap and water and rotated 180° and filled with 4 liters of clean sea water for the next trial.

| Killifish Preference Data (0.2% Ethanol vs. 0.2% Ethanol + Firefly Lipids) Lipids from 20 g wet wt. Firefly in 20 mls ETOH. | | | |
|---|---|---|---|
| Fish # | % Time ETOH Only | % Time Firefly Lipid + ETOH | Flow Rate |
| 1 | 27 | 9 | 2 ml/min |
| 2 | 40.72 | 15.7 | 2 ml/min |
| 3 | 41.11 | 20 | 2 ml/min |
| 4 | 99 | 1 | 1 ml/min |
| 5 | 4 | 17.44 | 1 ml/min |

It wil be appreciated that the subject invention has very extensive practical use in protecting bathing zones from the invasion of objectionable sea life such as sharks. Additionally, it is clear that the compositions, which include suspensions of fresh fireflies, suspensions of lanterns of fireflies, lyophilized fireflies, and extracts of lyophilized fireflies, firefly components, and mixtures thereof may find more widespread utility in controlling and repelling many objectionable organisms including other marine life, birds, canines, cats and rodents, to prevent the invasion of such organisms into a zone to be protected.

In addition to aqueous dispersion and suspension compositions, the firefly material may be incorporated in petroleum base solvents or in emulsions of aqueous-non aqueous systems for application as fluid suspensions, fogs or aerosol sprays.

The invention now being fully described, it will be apparent to one with ordinary skill in the art that many changes and modifications can be made thereto without departing from the spirit and scope of the invention as set forth herein.

What is claimed as new and is intended to be secured by Letters Patent is:

1. A method of repelling insects, fish, birds and mammals comprising indroducing an effective amount of a repellent composition which comprises as the active ingredient aqueous dispersions of fireflies, suspensions of lanterns of fireflies, suspensions of fresh fireflies, suspensions of fireflies excluding lantern, organic solvent solutions of extracts of fireflies, dried fireflies, lyophilized fireflies or a mixture thereof, wherein said fireflies are of the genus Photinus, to the area from which said organisms are to be excluded.

2. The method of claim 1 wherein the active ingredient is an aqueous dispersion of fireflies.

3. The method of claim 1 wherein the active ingredient is selected from the group consisting of suspensions of fresh fireflies, suspensions of fireflies excluding laterns, suspensions of lanterns of fireflies and suspensions of firefly parts.

4. The method of claim 1 wherein the active ingredient is lyophilized fireflies.

5. The method of claim 1 wherein the active ingredient is dried frieflies.

6. The method of claim 1 wherein the active indgredient is organic solvent solutions of firefly extract.

7. The method of claim 6 wherein the organic solvent is a non-polar organic solvent.

8. The method of claim 7 wherein the non-polar orgainic solvent is selected from the group consisting of chloroform, 1,1,1,-trichloroethane, 1,1,2,2,-tetrachloroethane, carbontetrachloride, benzene, toluene and cyclohexane.

9. The method of claim 1 wherein the active ingredient is introduced in the form of a dust or spray.

10. The method of claim 1 wherein the firefly-derived composition is introduced in the form of an aqueous suspension active ingredient.

11. The method of claim 1 wherein the active ingredient is introduced in the form of a slow-release hydrophilic polymerized foam.

12. The method of claim 1 wherein the organisms repelled by the active ingredient are selected from the group consisting of insects, fish, birds, and mammals.

13. The method of claim 12 wherein the organisms repelled are insects.

14. The method of claim 12 wherein the organisms repelled are fish.

15. The method of claim 12 wherein the organisms repelled are birds.

16. The method of claim 1 wherein the organisms repelled are mammals.

* * * * *